United States Patent
Martino

(10) Patent No.: US 12,156,616 B2
(45) Date of Patent: Dec. 3, 2024

(54) WATER REMOVAL DEVICE FOR THE HUMAN BODY

(71) Applicant: Marc Gregory Martino, Westlake Village, CA (US)

(72) Inventor: Marc Gregory Martino, Westlake Village, CA (US)

(\*) Notice: Subject to any disclaimer, the term of this patent is extended or adjusted under 35 U.S.C. 154(b) by 806 days.

(21) Appl. No.: 17/126,464

(22) Filed: Dec. 18, 2020

(65) Prior Publication Data

US 2021/0186272 A1    Jun. 24, 2021

Related U.S. Application Data

(60) Provisional application No. 62/950,111, filed on Dec. 19, 2019.

(51) Int. Cl.
  *A47K 10/00* (2006.01)

(52) U.S. Cl.
  CPC .................... *A47K 10/00* (2013.01)

(58) Field of Classification Search
  CPC . A47L 1/06; A47L 13/11; A47L 13/12; A46B 5/02; A46B 17/08; B60S 3/002; A47K 7/028; B08B 9/08; A47J 42/288; A47J 43/288
  See application file for complete search history.

(56) References Cited

U.S. PATENT DOCUMENTS

| | | | | |
|---|---|---|---|---|
| 2,722,703 A | * | 11/1955 | Green | A46B 15/00 15/167.1 |
| 3,540,432 A | * | 11/1970 | Ayre | A61B 10/0291 604/35 |
| 5,137,030 A | * | 8/1992 | Darougar | A61B 10/02 600/570 |
| 5,487,203 A | * | 1/1996 | Brach, Jr. | G09F 23/00 40/586 |
| 5,875,516 A | * | 3/1999 | Blue | A46B 15/0097 248/688 |
| 6,935,767 B2 | * | 8/2005 | Nikkhah | A47J 43/0794 366/129 |
| D563,069 S | * | 2/2008 | Yovanovich | D32/54 |
| 10,258,193 B1 | * | 4/2019 | Reed | F23Q 2/16 |
| D1,002,299 S | * | 10/2023 | Wang | D7/682 |
| 2011/0179887 A1 | * | 7/2011 | Cobian | A61B 10/0291 73/864 |
| 2017/0238768 A1 | * | 8/2017 | Schull | A47K 7/028 |

FOREIGN PATENT DOCUMENTS

WO    WO-2005041643 A2 *    5/2005    ............. A01K 13/00

\* cited by examiner

*Primary Examiner* — Shay Karls
(74) *Attorney, Agent, or Firm* — Orbit IP LLP

(57) ABSTRACT

A water removal device is configured to remove residual water off a user after getting wet. A handle is configured to be held within a user's hand, the handle extending along a longitudinal axis between a bottom handle end to a top handle end. A wiping extension outwardly extends beyond the top handle end along the longitudinal axis from a proximal wiping extension end to a distal wiping extension end. The wiping extension has a plurality of wiping edges evenly disposed about the longitudinal axis and extending generally along the longitudinal axis. The entirety of the water removal device may be formed as a single contiguous part where it is made from an injection molded polymer.

17 Claims, 4 Drawing Sheets

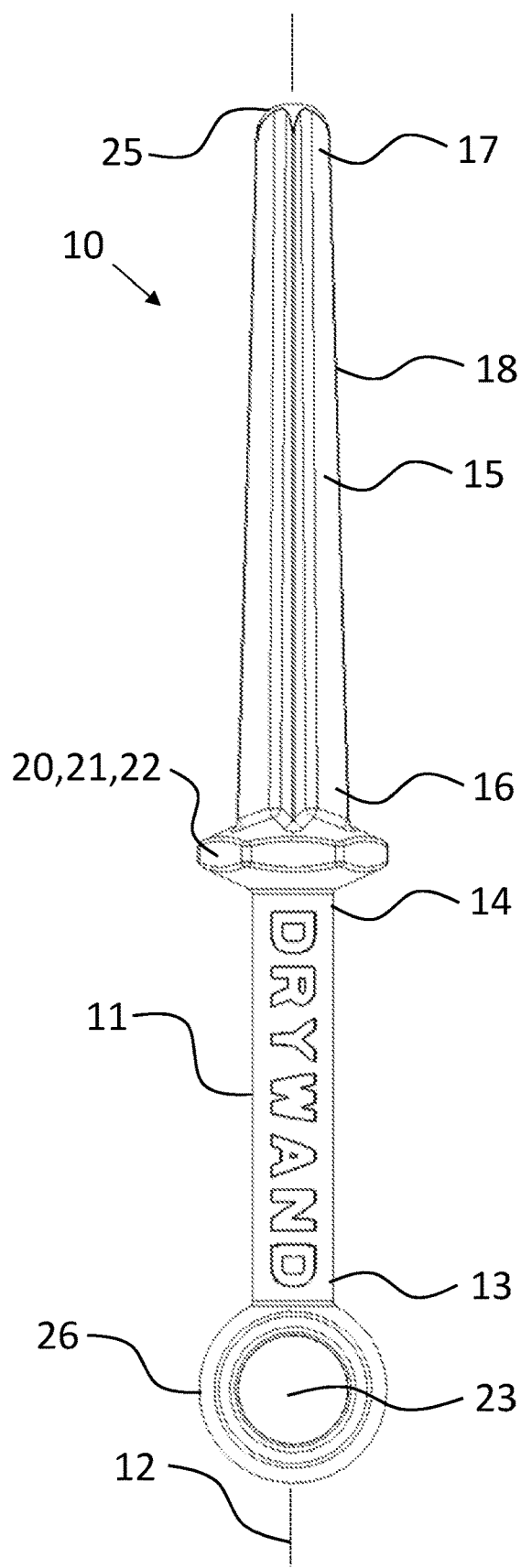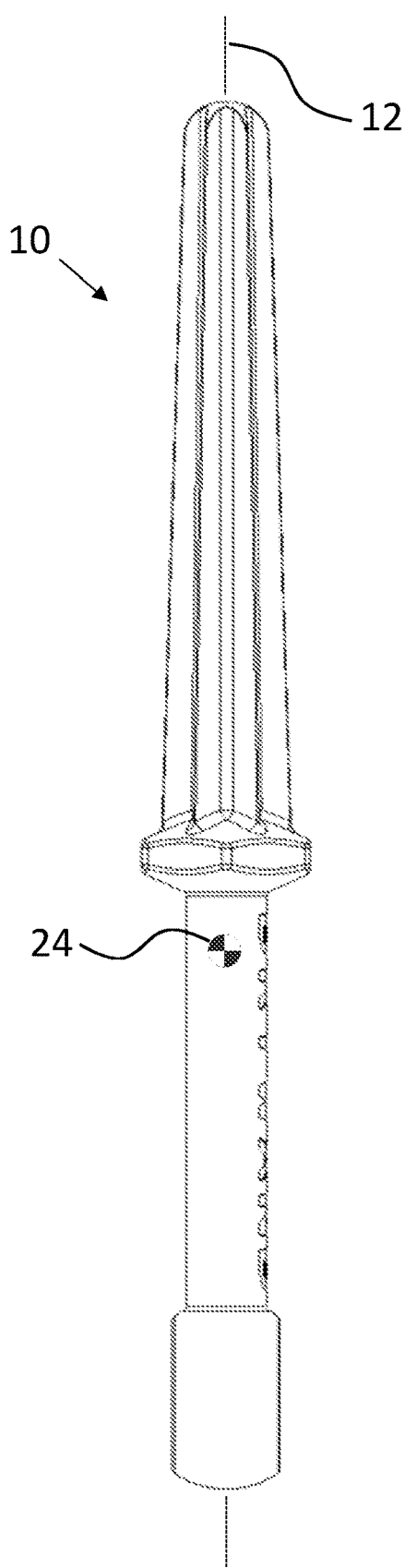
FIG. 3
FIG. 4

WATER REMOVAL DEVICE FOR THE HUMAN BODY

CROSS-REFERENCE TO RELATED APPLICATIONS

This application claims priority to provisional application 62/950,111 filed on Dec. 19, 2019, the entire contents of which are hereby incorporated in full by this reference.

DESCRIPTION

Field of the Invention

The present invention generally relates to bathing and showering. More particularly, the present invention relates to a body squeegee that is designed to easily and quickly remove a large portion of water before drying with a towel.

Background of the Invention

The following description for the background of the invention is based on the portion of the provisional application 62/950,111 filed on Dec. 19, 2020 in regards to the body squeegee, the contents of which are repeated herein below. It is noted that the rest of the contents of the '111 provisional in regards to the other inventions are also fully incorporated herein to maintain a consistent chain of disclosure to subsequent continuation and/or continuation-in-part applications covering these other inventions.

In regards to the provisional application No. 62/950,111, FIG. 1 is a perspective view of an exemplary body squeegee and associated suction cup hook. FIG. 2 is a side view of the structure of FIG. 1 in an exploded state. FIGS. 3A-D is taken from section 3A-D from FIG. 1 and are sectional views of different embodiments showing the plurality of edges for wiping water away. FIGS. 4A-F is taken from FIG. 3A showing enlarged sectional views of different embodiments of the contact edge of the wiper.

Having good personal hygiene is of critical importance for many people. Taking a bath or a shower is part of a normal hygiene regiment. However, taking multiple showers or bathes a day can create a couple problems. First, one's towel can become damp from a previous shower and remain damp by the time the person takes a second shower. Most people do not want to use a damp towel. A solution to a damp towel is to use multiple towels but this is also problematic. In either case, these towels will need to be laundered on a more than often basis. This leads to increase use of the laundry machine which utilizes a lot of water. It is often that parts of the country are in a drought and conservation of water is of high importance.

Another problem that people may experience is when going to the beach. It is common for beach goers to enter the water several times in the span of a couple hours. Using one's towel repeatedly at the beach quickly leads to a damp and wet towel. Then laying on such a towel on the beach becomes undesirable. Unfortunately, it still takes too long of a period of time for the towel to dry out making it ready to be used again. Also, carrying multiple towels is also burdensome and not a good solution.

Accordingly, there is a need for a better way to dry off after becoming wet. The present invention fulfills these needs and provides other related advantages.

The human squeegee shown in FIG. 1 includes a handle configured to be held within the human hand. An extension (best shown in FIG. 2) extends from the handle. The extension is cantilevered from the handle and aligned with a longitudinal axis of the handle. The handle and the extension can be made from a variety of known materials. However, plastic could be a good choice such that the handle and extension can be injection molded.

A resilient wiper extends along and covers at least a portion of the extension or the entirety of the extension. The wiper is made from a soft and flexible material such as rubber or silicon or the like. The softness and flexible material contacts the human body so it should not be too hard, yet also not be too soft such that it doesn't hold its unique shape.

As can be seen in FIG. 1 along with FIGS. 3A-D the cross section through the wiper is in a plane that is perpendicular to the longitudinal axis comprising a cross sectional outer surface that includes a plurality of points evenly distributed about the longitudinal axis. Said differently, the wiper comprises a plurality of longitudinally extended blades disposed circumferentially around the longitudinal axis. Said differently again, the wiper includes a plurality of longitudinally disposed edges evenly disposed about the longitudinal axis, wherein the plurality of edges comprises at least 3, 4, 5, 6, 7, 8, 9, 10, 11, 12 or more edges.

The unique shape of the wiper is designed to whisk/wipe water from the human skin when moved gently and quickly over it. This is similar to how a squeegee works on a car body, or on pavement. The edge of the wiper creates a barrier that removes the water without the need of a towel. As shown in FIGS. 1 and 2, the wiper can be tapered in shape as it extends along the at least portion of the extension.

The wiper can be made as a separate part and then assembled onto the extension. This allows the possibility that the wiper is removable and can be replaced over time when broken or degraded from use. Alternatively, the wiper can be over-molded such that it is permanently attached. To help keep the wiper in place, in FIG. 2 are shown varying stops that may be used to lock the wiper on the extension. For example an angle stop prevents the wiper from being removed but allows easy assembly. Other types of stops could be bumps, rectangular in shape or chamfered in shape. Alternatively not shown, the extension could have depressions or through holes that engage the wiper when assembled.

As can be seen in FIGS. 4, various types of edges can be used that vary from sharp edges (FIG. 4A), blunt edges (FIG. 4B), rounded edges (FIG. 4C), square or rectangular edges (FIG. 4D), angled-concave edges (FIG. 4E) or rounded-concave edges (FIG. 4F). While the edges are straight along the longitudinal axis, they can take many forms when views in cross-section.

The handle can also include a hole configured to accept a storage hook. The storage hook would be attached to a suction cup that can then be placed in a person's shower. This makes storing and using the body squeegee very convenient and easy.

Use of the body squeegee after a bath or a shower could reduce the amount of residual water left on the human body by more than 75%. This means a user's towel would be removing 75% less water from the person's body. This would drastically reduce the amount of dampness absorbed by the towel and would extend the laundry time needed to one's towel. Also, the extended length of the extension and wiper allows a person to easily reach hard to get areas on their backs and legs. Also, the symmetrical shape and plurality of edges means an edge will always be contacting the human body no matter which orientation or direction the user is holding the handle. This is a far superior design over prior designs and speed up the effectiveness of the body squeegee.

What could be claimed is as follows. A human squeegee, comprising: a handle configured to be held within the human hand; an extension extending from the handle, the extension being cantilevered from the handle aligned with a longitudinal axis of the handle; and a resilient wiper extending along and covering at least a portion of the extension. The human squeegee of claim 1, wherein a cross section through the wiper in a plane that is perpendicular to the longitudinal axis comprises a cross sectional outer surface that includes a plurality of points evenly distributed about the longitudinal axis. The wiper comprises a plurality of longitudinally extended blades disposed circumferentially around the longitudinal axis. The wiper is tapered in shape as it extends along the at least portion of the extension. The wiper includes a plurality of longitudinally disposed edges evenly disposed about the longitudinal axis, wherein the plurality of edges comprises at least 3, 4, 5, 6, 7, 8, 9, 10 or more edges. The wiper is over-molded onto the extension. The handle comprises a hole configured to accept a storage hook. A suction cup removably attachable to the handle. The resilient wiper comprises a rubber, a flexible polymer or silicone.

A further refinement of the body squeegee invention is shown in FIGS. 5-9. FIGS. 5 and 6 are isometric views. FIG. 7 is a top view and FIG. 8 is a rear view. FIG. 9 is a side view.

During testing of various designs, it was discovered that an all plastic (polymer) body squeegee could be made that utilized only one material throughout the entire structure. Previously, it was thought that the wiper portion should be made from a flexible material, such as a rubber or the like. However, during testing, it was discovered that the wiper portion could be made from polymer materials like ABS, polypropylene or polycarbonate. These are relatively hard plastics in comparison to the rubber material that one associates with a squeegee.

Utilizing a hard plastic for the wiper portion itself goes against common skill and knowledge in the art of designing squeegees. Typically when one is utilizing a normal squeegee, the squeegee is soft in comparison to the material it is abutting, such a glass window or pavement. However, when applied to the human body, the wiper portion can remain rigid while the human skin and body deflect about the wiper. In essence, the same wiping away of water is achieved when using a rigid wiper.

Therefore, this new embodiment is made fully of the plastic material and has no secondary elastomeric portion. This is also a benefit as water will not be able to hide between part interfaces such that mildew or mold could develop over time.

It is also noted that the edge of each blade of the wiper has a small radius. If one was to make the edge perfectly sharp, it could potentially cut the user. If one makes the edge too round, the wiping affect is diminished. Therefore, it is best that the radius be at or less than the following values: 0.020 inches, 0.015 inches, 0.010 inches, 0.005 inches. For example, it is easy to notice a difference of effectiveness of whisking between the radius of 0.020 inches and 0.015 inches. Therefore, the smaller the radius the better the product functions as it scrapes away the water. Accordingly, the smaller the diameter the better while still considering not making the edge too sharp. It is noted that during use, the edges are not too sharp to cause any discomfort.

It is also noted that this new embodiment also has a blunt distal tip where it has been rounded. This prevents the distal tip from having any portion that could pierce or injure a user.

It is also noted that the round disk at the center could have at least one flattened edge such that if the product was laid on its side, it would not roll away. Ideally, several edges would be formed such that the product would not roll away no matter how it was laid down.

It is also noted that at the end of the handle there is a large loop. This loop allows one to place a finger through for easier manipulation during use. Also, this loop can be used to hang the body squeegee from a suction cup stand, shower caddy or the like.

FIGS. 9A and 9B are actually pictures of the prototype that was made in the inventor's 3D printer. As can be seen, the edges along the middle portion are flattened such that the device would not roll away if placed down onto a flat surface. Also, the handle portion weights more than the wiper portion, such that the wiper portion remains in the air when the device is placed flat upon a table. It could also be advantageous to make the device from a clear polymer such as polycarbonate, which is also very shatter resistant and durable.

SUMMARY OF THE INVENTION

An embodiment of the water removal device (10) is configured to remove residual water off a user after getting wet, the water removal device comprising: a handle (11) configured to be held within a user's hand, the handle extending along a longitudinal axis (12) between a bottom handle end (13) to a top handle end (14); a wiping extension (15) outwardly extending beyond the top handle end along the longitudinal axis from a proximal wiping extension end (16) to a distal wiping extension end (17); wherein the wiping extension comprises a plurality of wiping edges (18) evenly disposed about the longitudinal axis and extending generally along the longitudinal axis.

In other exemplary embodiments, the entirety of the water removal device may be formed as a single contiguous part.

In other exemplary embodiments, the water removal device consists of an injection molded polymer such as ABS, polycarbonate, and the like.

In other exemplary embodiments, the plurality of wiping edges comprises at least 4 edges, at least 5 edges or at least 6 edges. Alternatively, the plurality of wiping edges may consist of 6 edges.

In other exemplary embodiments, between each pair of adjacent wiping edges of the plurality of wiping edges it may comprise an inwardly shaped channel (19) extending generally along the longitudinal axis.

In other exemplary embodiments, a guard (20) may be disposed between the handle and the wiping extension, the guard disposed at the top handle end and the proximal wiping extension end, the guard having a larger minimum diameter in comparison to both a maximum diameter of the handle and a maximum diameter of the wiping extension.

In other exemplary embodiments, an outer perimeter surface (21) of the guard may comprise a plurality of flat surfaces (22) contiguous to one another.

In other exemplary embodiments, a center of gravity (24) of the water removal device may be located within the handle and not in the wiping extension.

In other exemplary embodiments, the handle may extend a distance of at least 3.5 inches and wherein the wiping extension may extend a distance of at least 6 inches.

In other exemplary embodiments, each of the plurality of edges may have a radius equal to or less than 0.020 inches, 0.015 inches, 0.010 inches or 0.005 inches.

In other exemplary embodiments, a cross section taken through the wiping extension in a plane that is perpendicular to the longitudinal axis may be star shaped having at least 5 points.

In other exemplary embodiments, a cross section taken through the wiping extension in a plane that is perpendicular to the longitudinal axis may taper from a larger cross section near the proximal wiping extension end to a smaller cross section near the distal wiping extension end.

In other exemplary embodiments, the distal wiping extension end of the wiping extension may be rounded (25).

In other exemplary embodiments, a hole (23) may be disposed at the bottom handle end configured to accept a storage hook.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is a front view of the structure of FIG. 1;

FIG. 4 is a side view of the structure of FIG. 1;

DETAILED DESCRIPTION OF THE PREFERRED EMBODIMENTS

Figure 1:
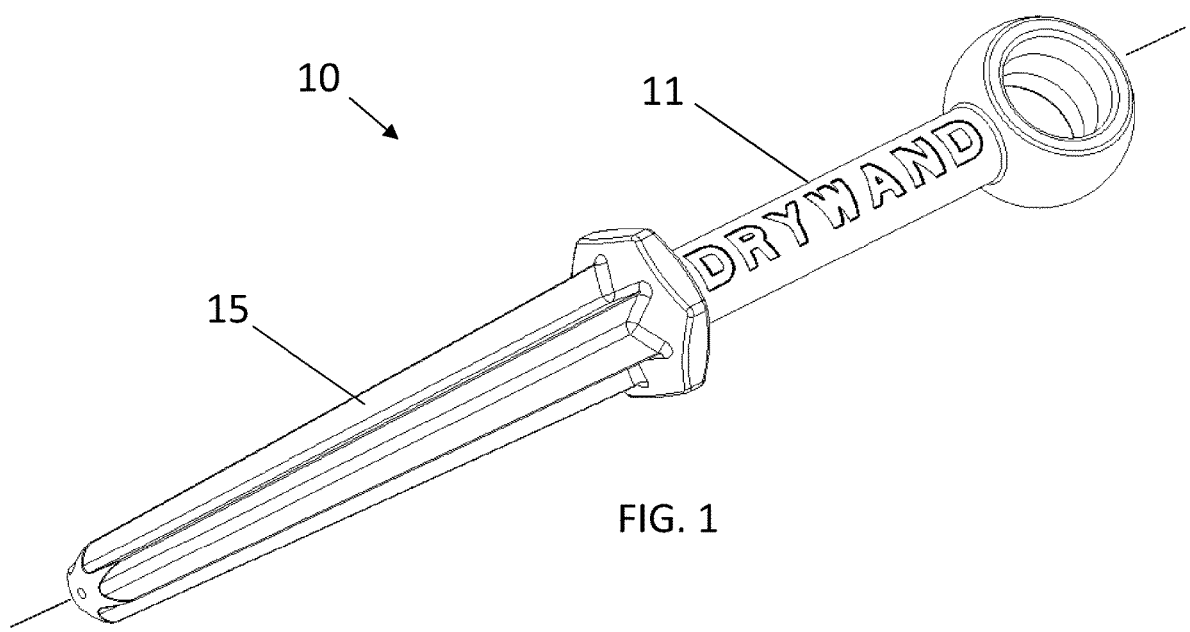
FIG. 1 is a perspective view of an embodiment of the present invention.
Figure 2:
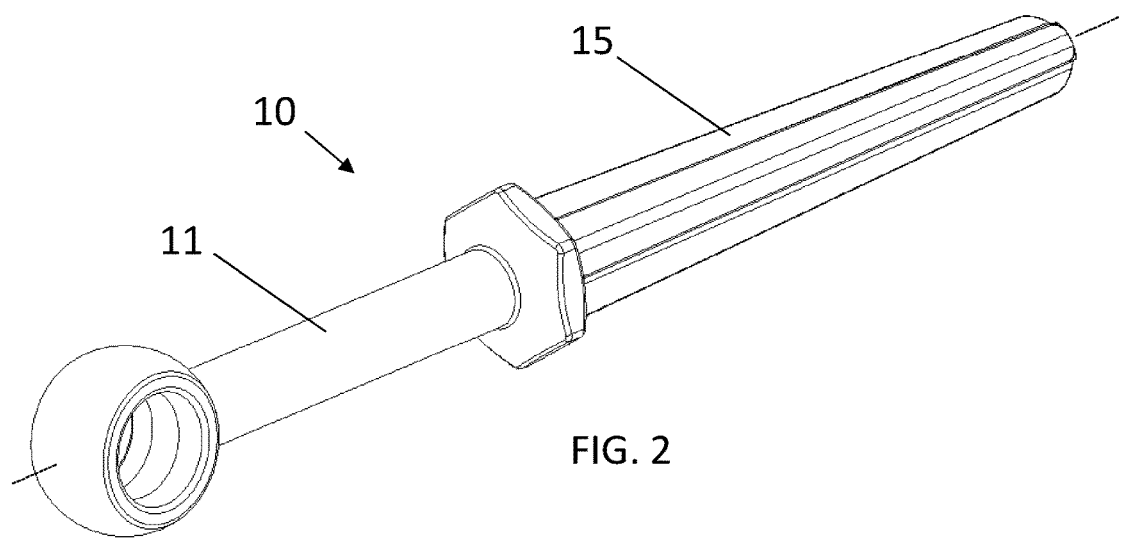
FIG. 2 is another perspective view of the structure of FIG. 1.
Figure 5:
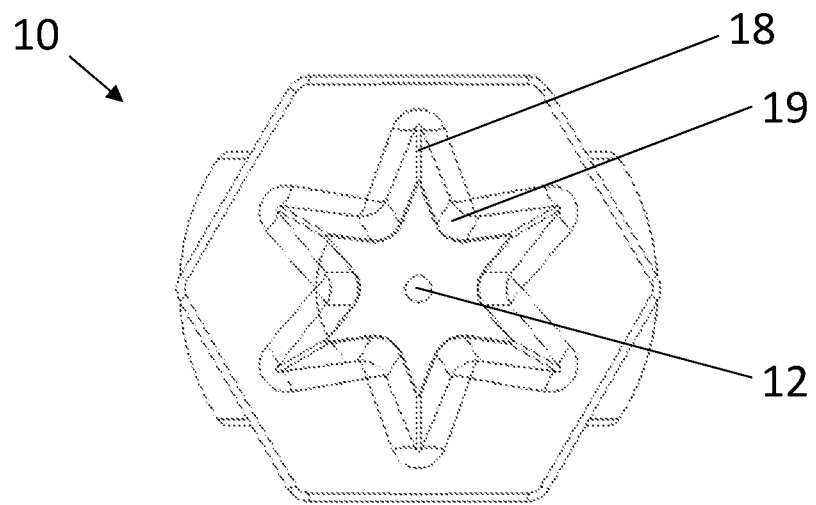
FIG. 5 is a top view of the structure of FIG. 1.
Figure 6:
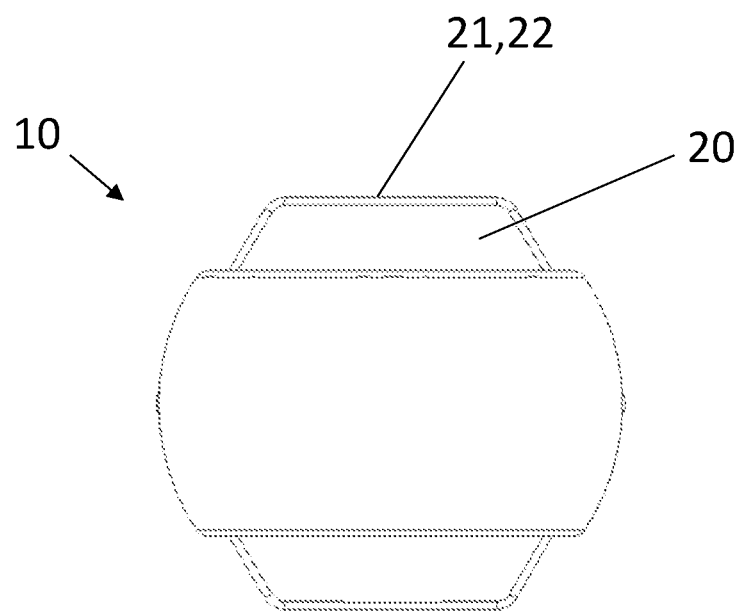
FIG. 6 is a bottom view of the structure of FIG. 1.
Figure 7:
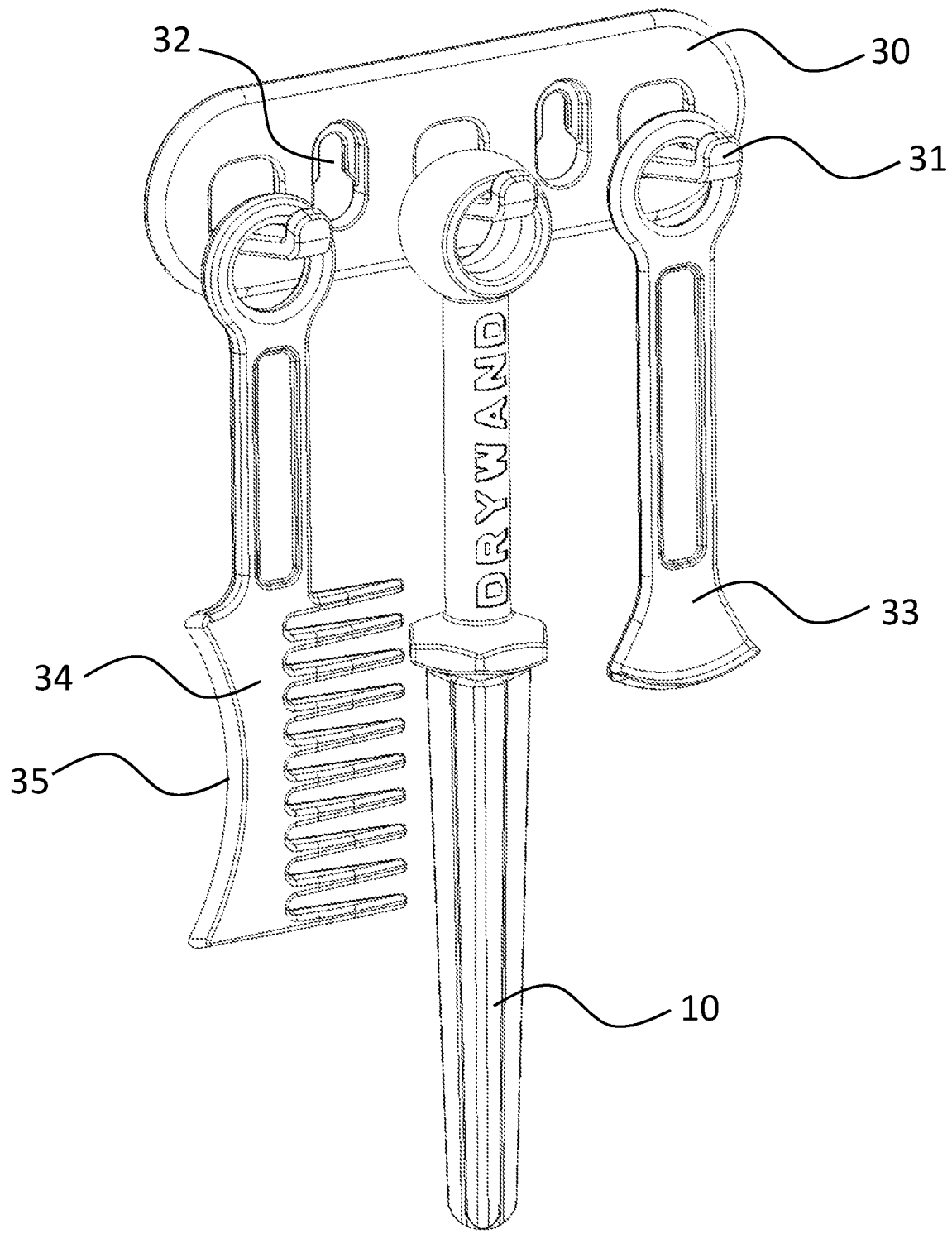
FIG. 7 is a perspective view of a cleaning kit containing the present invention.

As shown in the FIGS. 1-6 for purposes of illustration, the present invention for a water removal device 10 is referred to generally by the reference number 10. FIG. 7 shows a cleaning kit with the water removal device 10 that is configured to store within a shower in a space effective manner. Furthermore, to help interpreting FIGS. 1-7, the illustrations were made from a three dimensional computer aided drafting program where the tangent lines are showing as solid lines.

The water removal device 10 is configured to remove residual water off a user after getting wet, whether this be from the bath, shower, swimming pool, lake, ocean or the like. By removing a substantially large amount of water from the user's skin before a towel is used, it keeps the towel drier which in turn makes the towel more effective by staying drier. This also leads to less mold development within the towel over time and also reduced the need for laundry of the towel as often thus saving water overall.

The water removal device comprises a handle 11 configured to be held within a user's hand, the handle extends along a longitudinal axis 12 between a bottom handle end 13 to a top handle end 14. The handle may extend a distance of at least 3.5 inches but as shown here the handle is about 4 inches. 4 inches is a good length that will fit most hands of potential users. The diameter of the handle is about 0.75 inches, and again is a good diameter size for most users to grasp easily. It is understood by those skilled in the art that these dimensions could vary to some degree to allow for different designs while still keeping the intent of the present teaching.

As shown herein, the words DRYWAND are molded into the handle. The use of DRYWAND is just one potential marketing term and is not a critical aspect of the present invention, as no words are necessary for the device 10 to function appropriately. The diameter of the handle may also be larger or smaller without deviating from the scope of this teaching. Also, a texture of the surface of the handle may be used to help a user to grip the handle when in use.

A wiping extension 15 outwardly extends beyond the top handle end along the longitudinal axis from a proximal wiping extension end 16 to a distal wiping extension end 17. The wiping extension is the part of the device 10 that is used to make contact with the user's skin to whisk away residual water. The wiping extension comprises a plurality of wiping edges 18 evenly disposed about the longitudinal axis and extending generally along the longitudinal axis. The advantage of using a plurality of wiping edges 18 is that no matter how the user holds and positions the device 10 for use, at least one edge will make contact with the user's skin. This means one must not worry about the exact position of the device 10 in relation to the skin when used and dramatically simplifies use of the product while making it more effective at whisking away water.

Said differently, the wiping extension is star-shaped having a cross section taken through the wiping extension in a plane that is perpendicular to the longitudinal axis. This star-shape may have at least 4, 5, 6 or more points forming the edges 18. To facilitate an edge 18 always coming into contact with the user's skin, the plurality of wiping edges may comprise at least 4 edges, at least 5 edges or at least 6 edges or more. Alternatively, the plurality of wiping edges may consist of 6 edges.

The wiping extension may extend a distance of at least 6 inches. As shown here, the wiping extension is about 6.75-7 inches. For a smaller version, the wiping extension should at least be or more than 4 inches to make it effective when in use. For a larger version, the extension could be extended beyond 9 inches or the like, but if too long it can become hard to navigate in the small confines of a shower. Therefore a distance of about 7 inches has been shown to be very effective. In other words, the length of the wiping extension should be at or less than 9 inches such that it is easy to use in a small shower space.

In other exemplary embodiments, the entirety of the water removal device may be formed as a single contiguous part. For example, the water removal device may be made as an injection molded polymer such as ABS, polycarbonate, and the like. It was originally envisioned that a rubber like squeegee edge would be needed for the device. However, during testing, it was discovered that a hard plastic edge worked much better as it was the skin that would easily deform about the edge. This in turn allows the device to be made in a single injection molded shot which reduces costs and increases the durability and manufacturability of the device 10.

Between each pair of adjacent wiping edges of the plurality of wiping edges there is an inwardly shaped channel 19 extending generally along the longitudinal axis. The channel 19 allows a path for water to collect and reside after it is scraped off of the user's skin.

A guard 20 may be disposed between the handle and the wiping extension, the guard being disposed at the top handle end and the proximal wiping extension end. The guard serves several purposes. First, the guard is able quickly communicate to a user which portion should be grasped and which portion is intended to whisk water away. Second, the guard also prevents the hand from slipping down into the wiping extension 15 portion. Accordingly, it is best if the guard has a larger minimum diameter in comparison to both a maximum diameter of the handle and a maximum diameter of the wiping extension.

Third, the outer perimeter surface 21 of the guard may comprise a plurality of flat surfaces 22 contiguous to one another. If the device 10 is laid down on an angled surface, the flat surfaces 22 prevent the device from rolling away. This is helpful such that the device 10 does not fall down onto the shower floor where it could be stepped upon. As shown here, there are six flat surfaces 22, yet it is understood that any number of flat surfaces could be used ranging from 3 to more than 8 surfaces. Obviously, if too many surfaces 22 are used it would then approximate the shape of a circle and lose the ability to remain in position once laid upon a surface.

Fourth, a center of gravity 24 of the water removal device may be located within the handle and not in the wiping extension. This means that when the device is laid down, the handle portion will fall to make contact with the ground and the wiping extension portion will remain cantilevered in the air, thus allowing it to dry more quickly. In other words, the center of gravity 24 is below the guard to the side of the handle and not to the side of the wiping extension.

In regards to each of the plurality of edges, they may have a radius equal to or less than 0.020 inches, 0.015 inches, 0.010 inches or 0.005 inches. The smaller the radius, the sharper the edge becomes which in turn better whisks away the water. These radius are not sharp enough to cut one's skin while in use but do effectively whisk away water.

As can be seen in the figures, a cross section taken through the wiping extension in a plane that is perpendicular to the longitudinal axis tapers from a larger cross section near the proximal wiping extension end to a smaller cross section near the distal wiping extension end. The taper is best seen in FIGS. 3 and 4 where one can see the taper of the wiping extension getting smaller as it gets closer to the distal wiping extension end 17. This taper is for aesthetic purposes as it is not necessarily needed, but does seem to be helpful for use as improving the balance of the device when held in a user's hand.

Furthermore, to make sure the distal wiping extension end 17 does not have any sharp edges that could be scraped or stabbed into the user during use, the distal wiping extension end 17 of the wiping extension may be rounded 25. This rounding 25 of the edges 18 at the end 17 increases the safety and comfort of the device and is a critical feature.

To aid in storage of the device 10, a hole 23 may be disposed at the bottom handle end configured to accept a storage hook. As shown herein, the hole is part of a larger ring feature 26. The ring feature 26 helps to define the bottom of the handle 11 and prevents the device from slipping out of one's hand. Furthermore, a user can actually place a finger through the hole 23 if they prefer for use.

The use of a storage hook is best seen in FIG. 7 which shows an assembly utilizing the device 10. A shower wall bracket 30 has a plurality of hooks 31 such that the device 10 may be hung for storage. Holes 32 allow suction cups (not shown) to be engaged and captured such that the suction cups hold the bracket 30 to the wall of the shower. The bracket has three hooks 31 such that now a tongue scraper 33 and a hair detangler 34 can be added for increased functionality. The hair detangler also includes a single concave wiping edge 35 meant to press against one's scalp and hair such that water can be most easily wiped from the hair along the top of the head.

Now, while taking a shower one can use the tongue scraper while in the shower as this is a very convenient time and location for such use. Then, after the shower is over, one can take about 5 second to use the hair detangler 34 to remove a large portion of water trapped in the hair along the scalp. Finally, one can take about thirty seconds to a minute to wipe any residual water with the device 10. As taught before, this removes a large portion of the water such that one's towel remains drier, which makes the towel more effective, keeps the towel fresher and reduces mold development in the towel. This in turn reduces the need to launder the towel as often.

Although several embodiments have been described in detail for purposes of illustration, various modifications may be made to each without departing from the scope and spirit of the invention. Accordingly, the invention is not to be limited, except as by the appended claims.

What is claimed is:

1. A water removal device configured to remove residual water off a user after getting wet, the water removal device comprising:
    a handle configured to be held within a user's hand, the handle extending along a longitudinal axis between a bottom handle end to a top handle end;
    a wiping extension outwardly extending beyond the top handle end along the longitudinal axis from a proximal wiping extension end to a distal wiping extension end;
    wherein the wiping extension comprises a plurality of wiping edges evenly disposed about the longitudinal axis and extending generally along the longitudinal axis;
    wherein the plurality of wiping edges comprises at least 5 edges;
    wherein between each pair of adjacent wiping edges of the plurality of wiping edges comprises an inwardly shaped channel extending generally along the longitudinal axis;
    wherein each wiping edge of the plurality of wiping edges are straight as they extend from the proximal wiping extension end to the distal wiping extension end;
    wherein the wiping extension is longer in length along the longitudinal axis in comparison to the handle.

2. The water removal device of claim 1, wherein the entirety of the water removal device is formed as a single contiguous part.

3. The water removal device of claim 2, wherein the water removal device consists of an injection molded polymer.

4. The water removal device of claim 1, wherein the plurality of wiping edges comprises at least 6 edges.

5. The water removal device of claim 1, wherein the plurality of wiping edges consists of 6 edges.

6. The water removal device of claim 1, wherein a guard is disposed between the handle and the wiping extension, the guard disposed at the top handle end and the proximal wiping extension end, the guard having a larger minimum diameter in comparison to both a maximum diameter of the handle and a maximum diameter of the wiping extension.

7. The water removal device of claim 6, wherein an outer perimeter surface of the guard comprises a plurality of flat surfaces contiguous to one another.

8. The water removal device of claim 7, wherein a center of gravity of the water removal device is located within the handle and not in the wiping extension.

9. The water removal device of claim 1, wherein the handle extends a distance of at least 3.5 inches and wherein the wiping extension extends a distance of at least 6 inches.

10. The water removal device of claim 1, wherein each of the plurality of edges has a radius equal to or less than 0.020 inches.

11. The water removal device of claim 1, wherein a cross section taken through the wiping extension in a plane that is perpendicular to the longitudinal axis is star-shaped having at least five points forming the plurality of edges.

12. The water removal device of claim 1, wherein a cross section taken through the wiping extension in a plane that is perpendicular to the longitudinal axis tapers from a larger cross section near the proximal wiping extension end to a smaller cross section near the distal wiping extension end.

13. The water removal device of claim 1, wherein the distal wiping extension end of the wiping extension is rounded.

14. The water removal device of claim 1, wherein a hole is disposed at the bottom handle end configured to accept a storage hook.

15. A water removal device configured to remove residual water off a user after getting wet, the water removal device comprising:
- a handle configured to be held within a user's hand, the handle extending along a longitudinal axis between a bottom handle end to a top handle end;
- a wiping extension outwardly extending beyond the top handle end along the longitudinal axis from a proximal wiping extension end to a distal wiping extension end;
- wherein the wiping extension comprises a plurality of wiping edges evenly disposed about the longitudinal axis and extending generally along the longitudinal axis;
- wherein each wiping edge of the plurality of wiping edges are straight as they extend from the proximal wiping extension end to the distal wiping extension end;
- wherein the plurality of wiping edges comprises at least 5 edges;
- wherein between each pair of adjacent wiping edges of the plurality of wiping edges comprises an inwardly shaped channel extending generally along the longitudinal axis;
- wherein the wiping extension is longer in length along the longitudinal axis in comparison to the handle;
- wherein the entirety of the water removal device is formed as a single contiguous part; and
- wherein the water removal device is an injection molded polymer.

16. A water removal device configured to remove residual water off a user after getting wet, the water removal device comprising:
- a handle configured to be held within a user's hand, the handle extending along a longitudinal axis between a bottom handle end to a top handle end;
- a wiping extension outwardly extending beyond the top handle end along the longitudinal axis between a proximal wiping extension end to a distal wiping extension end;
- wherein the wiping extension comprises a plurality of wiping edges evenly disposed about the longitudinal axis and extending generally along the longitudinal axis;
- wherein between each pair of adjacent wiping edges of the plurality of wiping edges comprises an inwardly shaped channel extending generally along the longitudinal axis;
- wherein a guard is disposed between the handle and the wiping extension, the guard disposed at the top handle end and the proximal wiping extension end, the guard having a larger minimum diameter in comparison to both a maximum diameter of the handle and a maximum diameter of the wiping extension;
- wherein an outer perimeter surface of the guard comprises a plurality of flat surfaces contiguous to one another; and
- wherein a center of gravity of the water removal device is located within the handle and not in the wiping extension.

17. The water removal device of claim 16, wherein a cross section taken through the wiping extension in a plane that is perpendicular to the longitudinal axis tapers from a larger cross section near the proximal wiping extension end to a smaller cross section near the distal wiping extension end.

* * * * *